United States Patent [19]

Acken

[11] Patent Number: 5,509,928
[45] Date of Patent: Apr. 23, 1996

[54] INTERNALLY SUPPORTED SELF-SEALING SEPTUM

[75] Inventor: Alfred D. Acken, Sylmar, Calif.

[73] Assignee: Pacesetter, Inc., Sylmar, Calif.

[21] Appl. No.: 398,581

[22] Filed: Mar. 2, 1995

[51] Int. Cl.[6] ................................... A61N 1/375
[52] U.S. Cl. ............................. 607/037; 439/909
[58] Field of Search ................... 607/37, 36; 439/909

[56] References Cited

U.S. PATENT DOCUMENTS 4,479,489  10/1984  Tucci ............................. 607/37

FOREIGN PATENT DOCUMENTS 0342392  11/1989  European Pat. Off. ............... 607/37

*Primary Examiner*—William E. Kamm
*Assistant Examiner*—Kennedy J. Schaetzle
*Attorney, Agent, or Firm*—Malcolm J. Romano

[57] ABSTRACT

A self-sealing septum for isolating the setscrew used to secure a pacing lead connector pin to an implantable medical device such as a cardiac pacemaker. The septum comprises a generally cylindrical elastomer body having a central axis and a self-sealing passage coaxial with the axis for receiving a tool such as a hex key for driving the setscrew. The body of the septum contains a generally ring-shaped stiffener element for providing internal support and preventing damage to the septum passage caused by insertion of the hex key.

13 Claims, 3 Drawing Sheets

INTERNALLY SUPPORTED SELF-SEALING SEPTUM

FIELD OF THE INVENTION

The present invention relates generally to implantable medical devices such as cardiac pacemakers and particularly to an improved insulating plug or septum for isolating the setscrew which retains the connector pin of a pacing lead within a connector pin receptacle formed in the pacemaker housing.

BACKGROUND OF THE INVENTION

Although it will become evident to those skilled in the art that the present invention is applicable to a variety of implantable medical devices utilizing pulse generators to stimulate selected body tissue, the invention and its background will be described in terms of a specific example of such devices, namely, cardiac pacemakers for providing precisely controlled stimulation pulses to the heart.

Present day cardiac pacemakers are typically designed to be implanted in a "pocket" of fatty tissue near the patient's upper breast or lower abdomen. Accordingly, the electronic circuits within the pacemaker are hermetically sealed within a housing made of a material compatible with body tissue. Electrical connection is made with the pacemaker electronic circuits via feedthrough terminals that pass through the hermetically sealed housing. The feedthrough terminals are electrically connected to a connector receptacle in the pacemaker housing for receiving a connector pin at the proximal end of a pacing lead. The lead has a distal end having electrodes attached to the desired tissue location. For cardiac pacing, such a lead is typically inserted through one of the main veins of the patient, for example, the superior vena cava so that the distal end of the lead is directed inside the heart.

Good electrical contact must be maintained between the connector pin at the proximal end of the pacing lead and the pacing lead receptacle on the pacemaker. Further, the connection must be secure so that it does not come apart during use yet it must be detachable in the event the pacemaker or lead needs to be replaced. Moreover, the connection must at all times remain insulated and sealed from body fluids; such fluids are conductive and could cause an electrical short if permitted to infiltrate the connector assembly.

After pacing lead fixation, and before the pacemaker is connected, a final check is made with X-ray to insure that the entire intravascular part of the lead is correctly positioned. The connector pin at the proximal end of the pacing lead is then connected to the pacemaker by inserting it in the connector pin receptacle and pushing the connector pin all the way into the receptacle. Use of the correct connector pin (or connector pin adapter) assures that the connector pin makes a tight fit in the receptacle.

The connector pin is secured within the connector pin receptacle and good electrical contact between the pin and receptacle is assured by means of a setscrew received by a threaded opening in the pacemaker housing. The tightened setscrew is recessed within the threaded opening and is isolated electrically and from body fluids by an insulative (for example, rubber) sealing plug which, in accordance with one example of the prior art, is inserted in the portion of the threaded opening over the setscrew. In accordance with another example of the prior art, the setscrew is covered by an insulative plug comprising a self-sealing septum having a normally sealed passage in the center for receiving a hex key or wrench for turning the setscrew. Insertion of the hex key into the septum passage pushes the septum rubber into the hex cavity of the setscrew. Besides preventing full insertion of the hex key, the rubber tends to become pinched between the hex key and the sharp edges of the hex cavity resulting in shearing of the rubber and accumulation of rubber particles in the screw hex cavity. Further, the damage to the septum passage can destroy the integrity of the seal resulting in leakage of bodily fluids into the threaded setscrew opening which can cause electrical malfunctioning of the pacemaker. Further, damage to the septum passage can result in rubber particles entering the bodily cavity or pocket in which the implantable medical device is carried.

Accordingly, it is an overall object of the present invention to provide a septum-type insulating plug which overcomes the aforesaid problems.

Specifically, it is an object of the present invention to provide a septum-type insulation plug constructed so as to allow full insertion of the hex key while preventing damage to the plug and resulting leakage and dislodgement of rubber particles from the septum.

SUMMARY OF THE INVENTION

In accordance with the broad aspects of the present invention, there is provided an internally reinforced, self-sealing septum for isolating the setscrew used to secure the connector pin of the pacing lead of an implantable medical device. Pursuant to a specific exemplary embodiment of the invention, the septum comprises a generally cylindrical elastomeric body having a central axis and including a self-sealing passage, coaxial with the axis, for receiving a hex key for driving the setscrew. The body of the septum contains a generally ring-shaped stiffener element positioned substantially coaxial of the axis, the stiffener element preventing damage to the septum as a result of insertion of the setscrew driving tool in the septum passage.

In accordance with other aspects of the invention, the stiffener ring may be made of a biocompatible metal such as stainless steel, and has a generally L-shaped cross-section. Alternatively, the stiffener ring may have a generally circular cross-section. The stiffener element may be conveniently molded in situ as part of the process used to fabricate the elastomeric septum.

Upon insertion of a hex key into the self-sealing passage of the septum, the ring-shaped stiffener element provides internal support for the soft rubber septum material around the self-sealing passage not only preventing "coring" damage and resulting leakage but also preventing rubber particles from entering the hex cavity of the setscrew.

In accordance with yet another aspect of the invention, the body of the septum includes an outer surface having a generally horizontal surface projecting outwardly therefrom. The projecting surface is adapted to engage a mating surface on the housing of the implantable medical device whereby the septum resists withdrawal from the housing.

BRIEF DESCRIPTION OF THE DRAWINGS

Further objects, advantages and features of the invention will become apparent from the detailed description of the preferred embodiments when read in conjunction with the accompanying drawings in which.

DESCRIPTION OF THE PREFERRED EMBODIMENT

The following description presents the best mode contemplated for practicing the invention. This description is not to be taken in a limiting sense but is made merely for the purpose of describing the general principles of the invention the scope of which is defined by the appended claims.

The present invention will be explained with reference to the above-described figures, wherein like numerals are used to represent like parts or elements throughout.

Figure 1:
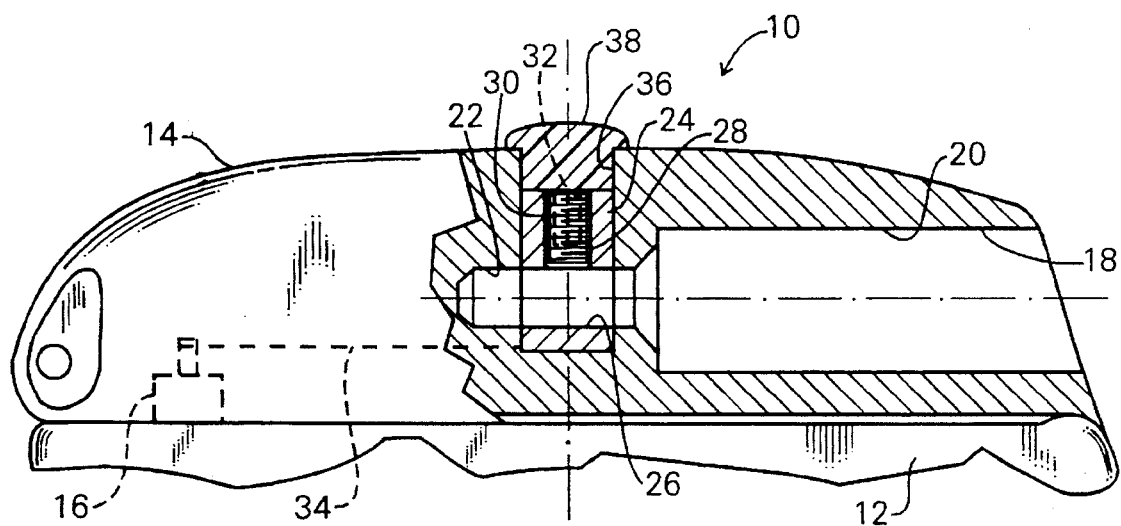
FIG. 1 is a side elevation view, partly in section, of the header assembly of a typical, prior art unipolar cardiac pacemaker showing a connector pin setscrew and a prior art sealing plug over the setscrew.

Referring first to FIG. 1, there is shown a portion of a prior art unipolar cardiac pacemaker 10 which includes a hermetically sealed housing 12 enclosing the pacemaker electronic circuits and battery. The pacemaker 10 includes a header assembly 14 which may be made of insulative material and which encloses a feedthrough terminal 16 for making electrical contact with the pacemaker electronic circuits within the housing 12. In some pacemaker models, the sealed housing 12—frequently referred to as the pacemaker "can"—is made from an electrically conductive material, and electrical contact may thus also be made through an exposed, noninsulated portion of the conductive material of the "can".

The header assembly 14 defines a longitudinally extending connector receptacle 18 for receiving a connector pin at the proximal end of a pacing lead (not shown). The receptacle 18 includes a main portion 20 and a smaller diameter portion 22 for receiving the tip electrode of the pacing lead. Molded into the header assembly 14 is a tip connector block 24 made from a conductive material, such as stainless steel, compatible with body fluids. The tip connector block 24 has a longitudinal hole or channel 26 in alignment with and of the same diameter as the tip receiving portion 22 of the receptacle 18. The tip electrode of the pacing lead is received in this channel when the pacing lead connector pin is fully inserted into the receptacle 18. The tip connector block 24 further includes a threaded hole 28 extending perpendicular to the channel 26 for receiving a setscrew 30. The setscrew 30 includes a hex cavity 32 for receiving a hex wrench or key (not shown in FIG. 1) for tightening or loosening the setscrew 30, all as well known in the art. Thus, with the tip electrode of the pacing lead in place within the tip receiving portion 22 of the receptacle 18, the setscrew 30 is tightened with a hex key in conventional fashion to firmly secure the tip electrode to the tip connector block 24 both mechanically and electrically. A conductive wire or ribbon 34 connects the tip connector block 24 with the feedthrough terminal 16.

In the prior art pacemaker example shown in FIG. 1, the tip connector block 24 is recessed within the header assembly 14 to define a blind hole 36 into which is inserted an insulative sealing plug 38 for isolating the setscrew electrically and protecting it from bodily fluids. It will be seen that in the arrangement illustrated in FIG. 1, it is necessary to remove the plug 38 in order to gain access to the setscrew 30 to tighten or loosen it.

Figure 2:
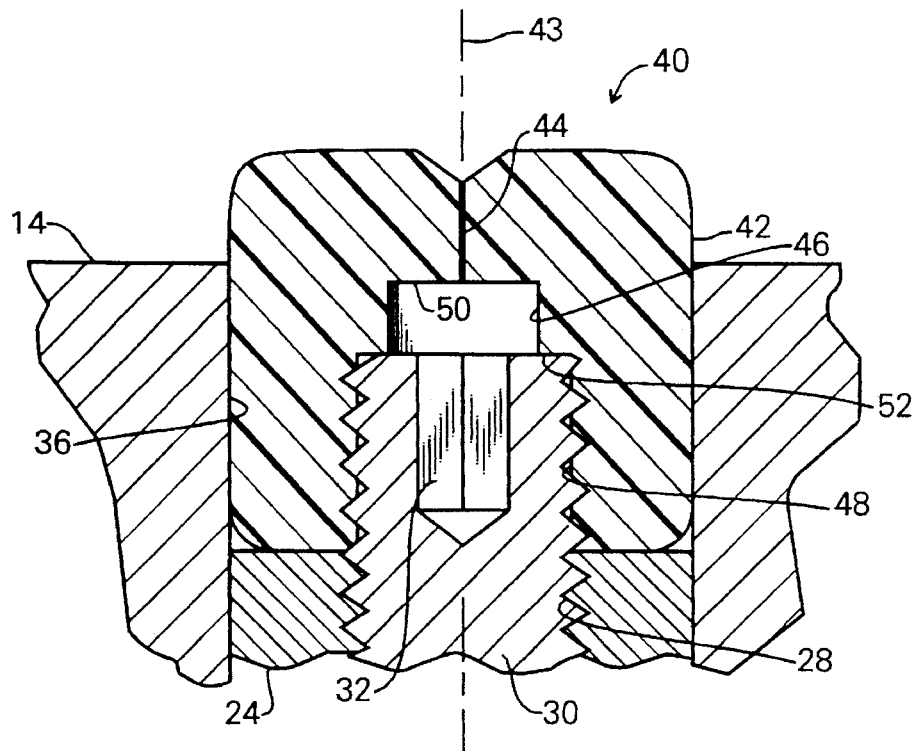
FIGS. 2 and 3 are side elevation views, in cross-section, of a portion of the header assembly of a cardiac pacemaker showing a self-sealing septum in accordance with the prior art.

FIG. 2 shows an alternative prior art setscrew isolating plug in the form of a self-sealing septum 40 of silicon rubber, for example, having an outer generally cylindrical surface 42, a central axis 43, and a central, normally sealed passage 44 for receiving a hex key insertable into the hex cavity 32 of the setscrew 30. The septum 40 is typically bonded in place within the hole 36 in the header 14. The septum 40 defines an internal, centrally disposed stepped bore comprising an upper recess or chamber 46 providing clearance for the tip of the hex wrench and a lower recess or chamber 48 having a larger diameter than the upper recess 46 and which provides clearance for the upper end of the setscrew 30. The upper chamber 46 is bounded by an upper wall 50 and the lower chamber 48 has an upper annular wall 52.

Figure 3:
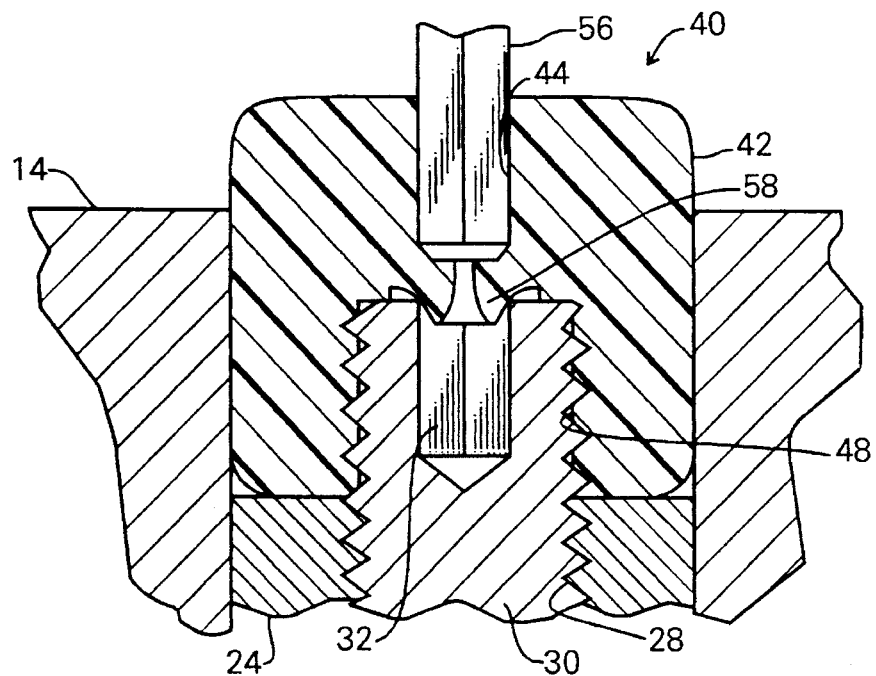

FIG. 3 illustrates the drawbacks of prior art septums of the type shown in FIG. 2. As a hex key 56 is inserted into the central passage 44, a portion 58 of the rubber septum material is pushed downwardly so that it is pinched between the tip of the hex key 56 and the edges of the hex cavity 32 in the setscrew 30. Besides the inability to seat the hex wrench within the hex cavity, this action causes shearing of the rubber at the hex cavity and consequent dislodgement of rubber particles which become trapped in the hex cavity of the setscrew. Further, the resulting "coring" of the septum passage destroys the sealing function of the passage. The resulting leakage can expose the setscrew to bodily fluids which can cause electrical malfunctioning of the pacemaker. Another disadvantage of the prior art septum illustrated in FIGS. 2 and 3 is that it can be pulled out of the blind hole 36 if it is not properly bonded.

Figure 4:
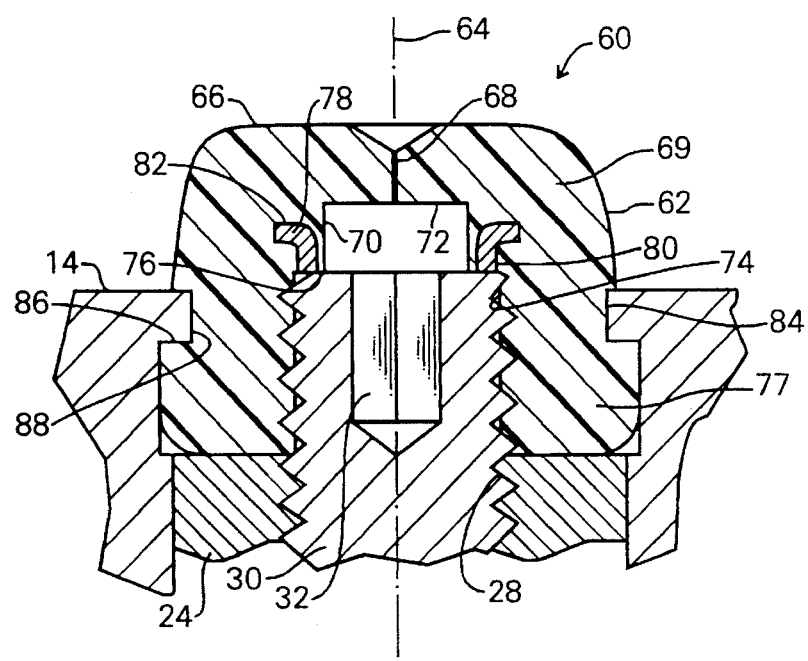
FIGS. 4 and 5 are side elevation views, in cross-section, of a portion of the header assembly of a unipolar cardiac pacemaker showing a self-sealing septum in accordance with a first embodiment of the present invention.
Figure 5:
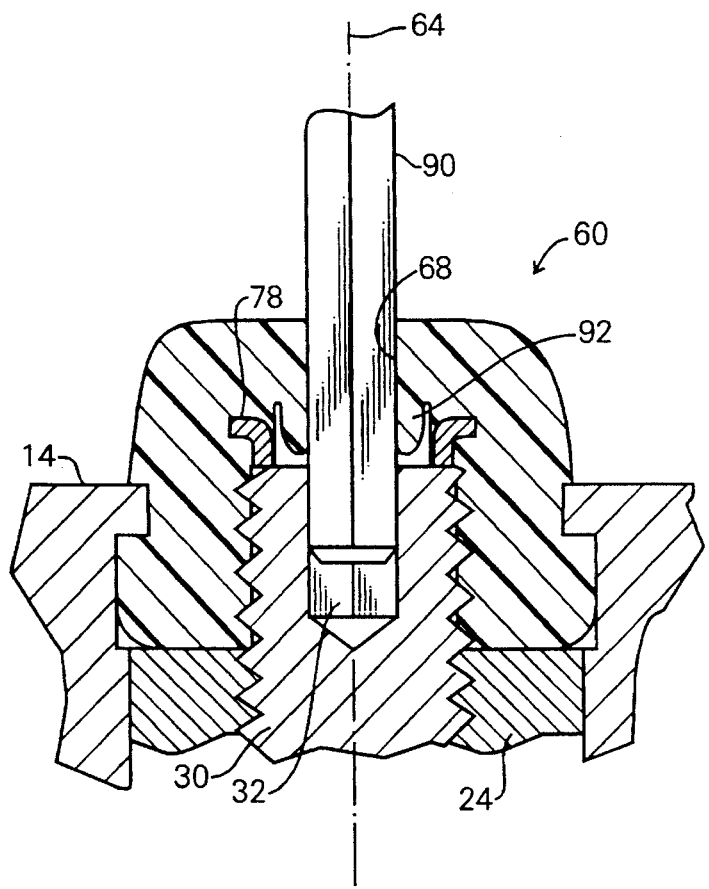

The present invention, a first embodiment of which is shown in FIGS. 4 and 5, solves the above-described problems. FIG. 4 shows a septum 60 of silicon rubber or the like having a cylindrical outer surface 62, a central axis 64, a top surface 66, and a central, self-sealing passage 68 for receiving a hex key or wrench. The passage 68 is disposed within an upper portion 69 of the septum. As in the prior art self-sealing septum shown in FIG. 2, the septum 60 includes a stepped bore comprising an upper cylindrical recess or chamber 70 having an upper horizontal wall 72, and a lower cylindrical recess or chamber 74 having an upper annular wall 76. The upper chamber 70 is positioned within the upper portion 69 of the septum 60, while the lower chamber 74 is disposed within a lower portion 77 of the septum. Both chambers 70 and 74 are coaxial with the axis 64, the passage 68 providing communication between the top surface 66 and the upper chamber 70.

Molded within the body of the septum 60 is a generally ring-shaped stiffener element 78 extending about the upper chamber 70 recess adjacent the upper annular wall 76 of the lower chamber 74. In the embodiment shown in FIG. 4, the stiffener element 78 is made of a biocompatible metal such as stainless steel and has a generally L-shaped configuration in cross-section comprising a vertical wall or flange 80 and an outwardly extending horizontal wall or flange 82.

The outer surface 62 of the septum 60 has an annular groove 84, defined in part by a generally horizontal annular surface 86, for receiving an inwardly projecting mating flange 88 on the header assembly 14.

The operation of the new septum is shown in FIG. 5. Upon insertion of a hex key 90 into the self-sealing passage 68, it will be seen that the stiffener element 78 provides internal support for the soft rubber septum material 92 around the central passage 68, not only preventing "coring" damage and resulting leakage but also preventing rubber from entering the hex cavity 32 of the setscrew 30.

The ring 78 is preferably molded in situ as part of the fabrication process of the septum 60. It will also be seen that the groove 84 in the outer surface of the septum securely locks the septum in place with the generally horizontal annular surface 86 preventing withdrawal thereof.

Figure 6:
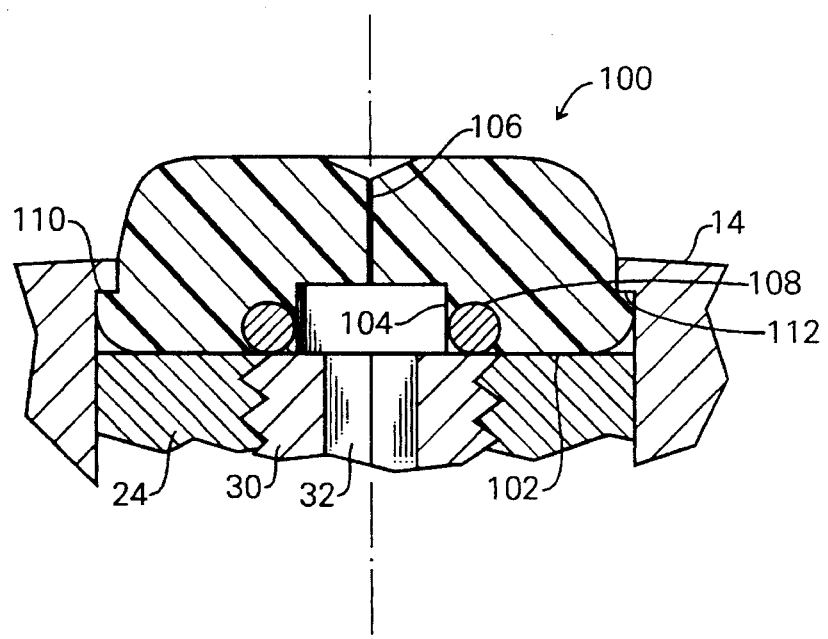
FIGS. 6 is a side elevation view, in cross-section, of a portion of the header assembly of a pacemaker showing a self-sealing septum in accordance with a second embodiment of the present invention.

FIG. 6 shows an alternative embodiment of the invention in the form of a "short" septum 100 having a bottom surface 102, a central, cylindrical recess or chamber 104 providing clearance for a hex key, and a self-sealing, central passage 106. Surrounding the chamber 104 recess adjacent the bottom surface 102 is a stiffener element in the form of a ring 108 having a circular cross-section. The ring 108 may be made of any relatively stiff biocompatible material such as stainless steel. As before, the stiffener ring 108 provides internal support for the septum material upon insertion of a hex key into the passage 106.

Projecting outwardly from the outer cylindrical surface of the septum 100 is an upwardly facing, horizontal surface 110 which engages a corresponding surface 112 on the header 14 thereby preventing withdrawal of the septum 100.

A stiffener element having an L-shaped cross-section, as in FIG. 4, can be used in the short septum embodiment of FIG. 6; conversely, a stiffener element having a circular cross-section can be used in the embodiment of FIG. 4. It will be further evident that stiffener elements having cross-sections other than circular or L-shaped can be used to obtain the advantages of the invention.

The pacemaker connector arrangement described herein is in terms of a unipolar pacing lead, that is, a pacing lead having a single conductor connected to the proximal tip electrode. However, it is to be understood that the invention also has applicability to bipolar pacing using dual conductor leads and to multi-polar pacing employing multiple conductor leads.

What is claimed is:

1. In an implantable medical device including a housing enclosing a receptacle for receiving a pacing lead connector pin, the receptacle including a connector block having a threaded aperture for receiving a setscrew for securing the connector pin to the connector block, a self-sealing septum adapted to be mounted on said housing for isolating the setscrew, the septum comprising a generally cylindrical elastomer body having a central axis and including a self-sealing passage coaxial with said axis for receiving a tool for driving the setscrew, the body of the septum containing a generally ring-shaped stiffener element positioned substantially coaxial of said axis, the stiffener element preventing damage to the septum as a result of insertion of the setscrew driving tool in the septum passage.

2. A septum, as defined in claim 1, in which the stiffener ring is made of metal.

3. A septum, as defined in claim 1, in which the stiffener ring has a generally L-shaped cross-section.

4. A septum, as defined in claim 1, in which the stiffener ring has a generally circular cross-section.

5. A septum, as defined in claim 1, in which the elastomer body comprises a molded structure and in which the stiffener element is molded in situ.

6. A septum, as defined in claim 1, in which the body of the septum comprises an outer surface, an upper portion and a lower portion, the upper portion including the self-sealing passage, the body further including a surface projecting outwardly from the outer surface of the body, the surface being adapted to cooperate with the housing of the implantable medical device to resist withdrawal of the septum from the housing.

7. In an implantable medical device including a housing enclosing a receptacle for receiving a pacing lead connector pin, the receptacle including a connector block having a threaded aperture for receiving a setscrew for securing the connector pin to the connector block, a self-sealing septum adapted to be mounted on said housing for isolating the setscrew, the septum comprising an elastomer body having a chamber for receiving the head portion of the setscrew, the chamber including an upper wall, the septum further including a self-sealing passage in said body in communication with the upper wall of the chamber for receiving a tool for driving the setscrew, the body of the septum containing a stiffener element adjacent the upper wall of the chamber, said stiffener element preventing damage to the septum as a result of insertion of the setscrew driving tool in the septum passage.

8. A septum, as defined in claim 7, in which the stiffener element comprises a stiffener ring.

9. A septum, as defined in claim 8, in which the stiffener ring is made of metal.

10. A septum, as defined in claim 8, in which the stiffener ring has a generally L-shaped cross-section.

11. A septum, as defined in claim 8, in which the stiffener ring has a generally circular cross-section.

12. A septum, as defined in claim 7, in which the elastomer body comprises a molded structure and in which the stiffener element is molded in situ.

13. A septum, as defined in claim 7, in which the body of the septum is generally cylindrical and has a central axis, the body comprising an outer surface, an upper portion and a lower portion, the upper portion including the self-sealing passage, the passage extending along the central axis, and the lower portion including the chamber, the chamber being generally cylindrical and coaxial with the central axis, the outer surface of the body having a groove adapted to receive a flange on the housing of the implantable medical device whereby the septum resists withdrawal from the housing.

\* \* \* \* \*